US012791544B2

(12) United States Patent
Almadan et al.

(10) Patent No.: US 12,791,544 B2
(45) Date of Patent: Nov. 10, 2026

(54) METHOD AND SYSTEM FOR DETERMINING ROCK OBJECTS IN PETROGRAPHIC DATA USING MACHINE LEARNING

(71) Applicant: ARAMCO SERVICES COMPANY, Houston, TX (US)

(72) Inventors: Ali Almadan, Houston, TX (US); Weichang Li, Katy, TX (US); Mustafa Ali H. Al Ibrahim, Safwa (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 582 days.

(21) Appl. No.: 18/459,238

(22) Filed: Aug. 31, 2023

(65) Prior Publication Data

US 2025/0076273 A1 Mar. 6, 2025

(51) Int. Cl.
*G01N 33/24* (2006.01)
*G06T 5/40* (2006.01)
(Continued)

(52) U.S. Cl.
CPC ............. *G01N 33/241* (2013.01); *G06T 5/40* (2013.01); *G06T 5/70* (2024.01); *G06V 10/50* (2022.01);
(Continued)

(58) Field of Classification Search
None
See application file for complete search history.

(56) References Cited

U.S. PATENT DOCUMENTS 11,425,852 B2 8/2022 Sibley et al.
2012/0281883 A1 11/2012 Hurley et al.
(Continued)

FOREIGN PATENT DOCUMENTS

CN 108985247 A 12/2018
CN 113506253 A 10/2021
(Continued)

OTHER PUBLICATIONS

Bozkir, A. S., et al. "Geological strength index prediction by vision and machine learning methods." ISRM EUROCK. ISRM, 2020. (Year: 2020).*
(Continued)

*Primary Examiner* — SJ Park
*Assistant Examiner* — Caroline E. Depalma
(74) *Attorney, Agent, or Firm* — Osha Bergman Watanabe & Burton LLP

(57) ABSTRACT

A method may include obtaining a petrographic image. The method may further include determining various region proposals based on the petrographic image and a selective searching function. A respective region proposal among the region proposals may correspond to various pixels in the petrographic image according to a predetermined dimension. The method may further include determining color histogram data for the petrographic image. The method may further include determining input image data based on the petrographic image, the region proposals, and the color histogram data. The method may further include determining a rock object using the input image data and a machine-learning model.

18 Claims, 10 Drawing Sheets

(51) Int. Cl.

| | |
|---|---|
| ***G06T 5/70*** | (2024.01) |
| ***G06V 10/50*** | (2022.01) |
| ***G06V 10/762*** | (2022.01) |
| ***G06V 10/764*** | (2022.01) |
| ***G06V 20/70*** | (2022.01) |

(52) U.S. Cl.

CPC .......... *G06V 10/762* (2022.01); *G06V 10/764* (2022.01); *G06V 20/70* (2022.01); *G06T 2207/10024* (2013.01); *G06T 2207/20081* (2013.01); *G06V 2201/07* (2022.01)

(56) References Cited

U.S. PATENT DOCUMENTS

| | | | | |
|---|---|---|---|---|
| 2015/0332471 | A1* | 11/2015 | Heo | G06T 7/11 382/103 |
| 2017/0032532 | A1* | 2/2017 | Andersen | G01N 23/04 |
| 2022/0207079 | A1 | 6/2022 | Shebl et al. | |
| 2022/0237891 | A1* | 7/2022 | Xu | G06V 10/507 |

FOREIGN PATENT DOCUMENTS

| | | | | | |
|---|---|---|---|---|---|
| WO | WO-2019246250 | A1 | * | 12/2019 | G06V 20/52 |
| WO | WO-2022011394 | A1 | * | 1/2022 | G01N 33/241 |

OTHER PUBLICATIONS

Deng, Jia et al., "ImageNet: A Large-Scale Hierarchical Image Database"; 2009 IEEE Conference on Computer Vision and Pattern Recognition; pp. 248-255; 2009 (8 pages).

Guo, Yandong et al., "MS-Celeb-1M: A Dataset and Benchmark for Large-Scale Face Recognition"; Computer Vision—ECCV 2016; Lecture Notes in Computer Science, vol. 9907; pp. 87-102; 2016 (16 pages).

Koeshidayatullah, Ardiansyah et al., "Fully automated carbonate petrography using deep convolutional neural networks"; Marine and Petroleum Geology; vol. 122, Article 104687; pp. 1-16; Dec. 2020 (16 pages).

Dunlop, Heather, "Automatic Rock Detection and Classification in Natural Scenes"; A thesis submitted in partial fulfillment of the requirements for the degree of Master of Science; CMU-RI-TR-06-40; Robotics Institute, Carnegie Mellon University; pp. 1-66; Aug. 2006 (74 pages).

Pasini, Andrea et al., "Adaptive Hierarchical Clustering for Petrographic Image Analysis"; Workshop Proceedings of the EDBT/ICDT 2019 Joint Conference; Mar. 26, 2019 (6 pages).

* cited by examiner

Petrographic Image A
401

METHOD AND SYSTEM FOR DETERMINING ROCK OBJECTS IN PETROGRAPHIC DATA USING MACHINE LEARNING

BACKGROUND

Petrography may be a branch of the science of petrology, which classifies and deciphers the origin of rocks as well as studies the relationships between various mineral deposits and effects of various geologic processes. In particular, petrography may use polarized-light microscopy to provide a nondestructive way to identify rock substances, such as crystalline or amorphous materials, with relatively high spatial resolution. As such, petrography may estimate chemical compositions of various rock samples as well as other geological properties.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes obtaining a petrographic image. The method further includes determining, by a computer processor, various region proposals based on the petrographic image and a selective searching function. A respective region proposal among the region proposals corresponds to various pixels in the petrographic image according to a predetermined dimension. The method further includes determining, by the computer processor, color histogram data for the petrographic image. The method further includes determining, by the computer processor, input image data based on the petrographic image, the region proposals, and the color histogram data. The method further includes determining, by the computer processor, a rock object using the input image data and a machine-learning model.

In general, in one aspect, embodiments relate to a system that includes an image acquisition system that includes a camera device and a reservoir simulator coupled to the image acquisition system. The reservoir simulator includes a computer processor and performs a method. The reservoir simulator acquires, using the image acquisition system, a petrographic image. The reservoir simulator determines various region proposals based on the petrographic image and a selective searching function. A respective region proposal among the region proposals corresponds to various pixels in the petrographic image according to a predetermined dimension. The reservoir simulator determines color histogram data for the petrographic image. The reservoir simulator determines input image data based on the petrographic image, the region proposals, and the color histogram data. The reservoir simulator determines a rock object using the input image data and a machine-learning model.

In some embodiments, a classified image is determined using a rock object and based on a petrographic image. A training dataset may be determined based on various classified images and the classified image. A machine-learning model may be obtained. The machine-learning model may be trained using the training dataset, various machine-learning epochs, and a supervised learning algorithm. In some embodiments, various petrographic images are obtained. Various region proposals may be determined based on the petrographic images and a selective searching function. Training data may be obtained that includes various classified images based on the petrographic images and the region proposals. A training operation may be performed on a machine-learning model using the training data. The machine-learning model may determine one or more predicted rock labels for a respective input petrographic image. The machine-learning model is updated iteratively until the one or more predicted rock labels satisfy a predetermined criterion. In some embodiments, color histogram data includes various histogram oriented gradients. A machine-learning model may be a support vector machine. The support vector machine may use the histogram oriented gradients and a kernel function to determine one or more rock objects.

In some embodiments, a selective search function determines a respective region proposal among various region proposals for an image object of interest within a respective petrographic image. The respective region proposal may correspond to a set of pixels that form a sub-image. In some embodiments, a selective search function is a hierarchical process based on one or more similarity measures that include a color metric, a texture metric, a size metric, and/or a shape metric. In some embodiments, various petrographic images are obtained. Various rock objects may be determined from the petrographic images using a machine-learning model. One or more image clusters may be determined using the rock objects and a clustering function. A training dataset may be determined based on the one or more image clusters. In some embodiments, a clustering function is an unsupervised machine-learning algorithm. In some embodiments, an edge smoothing operation is performed on a petrographic image to produce an adjusted petrographic image. Color histogram data may be determined using the adjusted petrographic image.

In some embodiments, a machine-learning model is an artificial neural network that includes an input layer, various hidden layers, and an output layer. In some embodiments, a petrographic image is acquired using a petrological microscope. In some embodiments, predicted data are determined for a geological region of interest using one or more petrographic images and a machine-learning model. The machine-learning model may be trained using a training dataset that includes a petrographic image and one or more rock objects. A presence of hydrocarbon deposits may be determined using the predicted data. In some embodiments, a system includes a drilling system a control system coupled to the drilling system and a reservoir simulator. The control system may transmit a command to the drilling system to perform a drilling operation based on predicted data for a geological region of interest. The predicted data may be determined using a trained model that is trained using a training dataset that includes a classified petrographic image corresponding to a petrographic image and one or more rock objects.

In light of the structure and functions described above, embodiments disclosed herein may include respective means adapted to carry out various steps and functions defined above in accordance with one or more aspects and any one of the embodiments of one or more aspect described herein.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
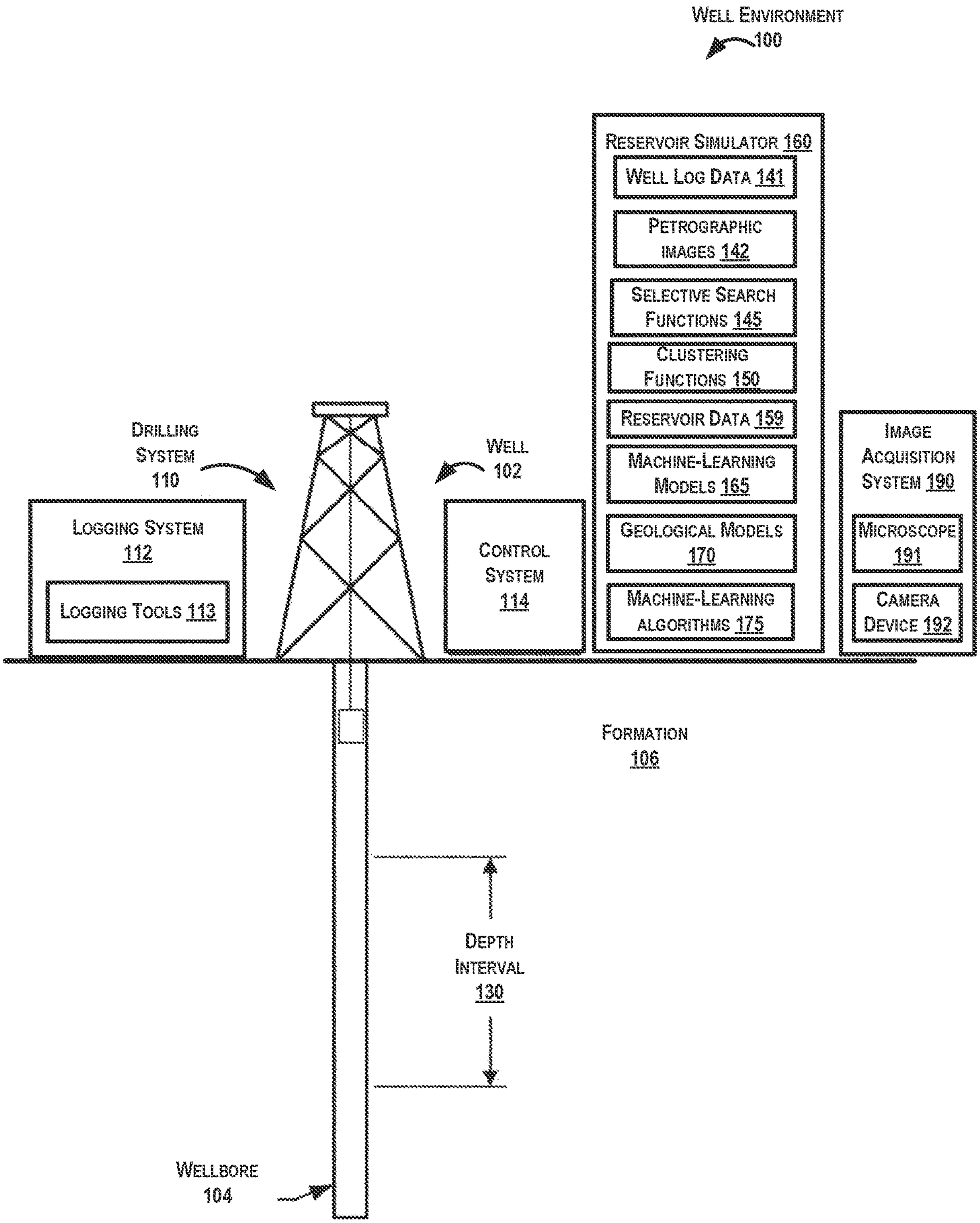
FIGS. 1 and 2 show systems in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for automatically identifying and extracting image objects (e.g., rock objects) from various images using machine learning. In some embodiments, for example, petrographic images are collected and analyzed for the presence of complete and/or partial rock objects using a machine-learning architecture. In particular, petrographic images may include images of various carbonate rocks from thin sections of core samples for use in a petrographic image analysis. While petrographic images are typically reviewed by geologists with extensive knowledge in petrography, identifying particular rock objects in an image collection may be a labor-intensive task that is also subject to inaccurate interpretation due to external factors. For example, a geologist may misclassify a portion of an image as including or lacking a rock specimen due to the quality of the image sample, the presence of many collided rocks, and the subjectivity of the reviewing geologist. Thus, some embodiments provide an automated framework that separates an image into multiple sub-images that correspond to different region proposals for analyzing whether a respective sub-image include a particular type of object.

Furthermore, a region proposal may correspond to one or more dimensions of pixels in an image (e.g., with respect to a particular length or width of a region of interest) that define boundaries of a sub-image. Additionally, image data for a particular region proposal may be subsequently analyzed using histogram oriented gradients (HOGs) as well as other similarity measures, such as the size or shape of certain objects within the image data. Likewise, image data may be preprocessed using image processing techniques, such as edge smoothing operations or color histogram techniques to determine various input image features within the image data for analysis by a machine-learning model. In some embodiments, for example, input image features are passed through one or more support vector machines in order to classify the image data as particular image object. Examples of image objects may include whether the image data includes a complete rock object, a partial rock object, or no rock objects.

Moreover, some embodiments are used to provide a structured dataset that is benchmarked with identified individual image objects (e.g., rock objects from carbonate rock thin sections). Using this machine-learning workflow, a large volume of annotated benchmark data may be generated without extensive labor-intensive labeling, such as for rock sample classification and rock property prediction. A well-structured dataset may subsequently be generated for use as training data and/or testing data in various machine-learning applications and evaluations. In particular, deep machine learning has come a long way in solving many technical problems with robustness and accuracy, where the machine-learning models are provided with sufficient and representative training data. Because deep machine learning may require huge amounts of training data, especially for computer vision-related tasks, some embodiments obtain training image data from multiple data sources, such as publicly-available image repositories and scientific journal resources. However, training data may require accurate object labeling and classification prior to being used in a training operation. Accordingly, different tasks based on machine learning may remain unsolvable and infeasible due to lack of available image data for training, which is especially prevalent in the petrography domain. For comparison, the study of palynological has a similar image object classification problem, where identifying different species and estimating thermal maturity may require the examination of thousands of organic matter particles in a single image.

Turning to FIG. 1, FIG. 1 shows a schematic diagram in accordance with one or more embodiments. As shown, FIG. 1 illustrates a well environment (100) that may include a well (102) having a wellbore (104) extending into a formation (106). The wellbore (104) may include a bored hole that extends from the surface into a target zone of the formation (106), such as a reservoir. The formation (106) may include various formation characteristics of interest, such as formation porosity, formation permeability, resistivity, density, water saturation, and the like. Porosity may indicate how much space exists in a particular rock within an area of interest in the formation (106), where oil, gas, and/or water may be trapped. Permeability may indicate the ability of liquids and gases to flow through the rock within the area of interest. Resistivity may indicate how strongly rock and/or fluid within the formation (106) opposes the flow of electrical current. For example, resistivity may be indicative of the porosity of the formation (106) and the presence of hydrocarbons. More specifically, resistivity may be relatively low for a formation that has high porosity and a large amount of water, and resistivity may be relatively high for a formation that has low porosity or includes a large amount of hydrocarbons. Water saturation may indicate the fraction of water in a given pore space.

Keeping with FIG. 1, the well environment (100) may include a reservoir simulator (160) and various well systems, such as a drilling system (110), a logging system (112), a control system (114), and a well completion system (not shown). The drilling system (110) may include a drill string, drill bit, a mud circulation system and/or the like for use in boring the wellbore (104) into the formation (106). The control system (114) may include hardware and/or software for managing drilling operations and/or maintenance operations. For example, the control system (114) may include one or more programmable logic controllers (PLCs) that include hardware and/or software with functionality to control one or more processes performed by the drilling system (110). Specifically, a programmable logic controller may control valve states, fluid levels, pipe pressures, warning alarms, and/or pressure releases throughout a drilling rig. In particular, a programmable logic controller may be a ruggedized computer system with functionality to withstand vibrations, extreme temperatures, wet conditions, and/or dusty conditions, for example, around a drilling rig. Without loss of generality, the term "control system" may refer to a drilling operation control system that is used to operate and control the equipment, a data acquisition and monitoring system that is used to acquire equipment data and to monitor one or more well operations, or a well interpretation software system that is used to analyze and understand well events, such as drilling progress. A logging system may be similar to a control system with a specific focus on managing one or more logging tools.

Turning to the reservoir simulator (160), a reservoir simulator (160) may include hardware and/or software with functionality for storing and analyzing well log data (141), such as borehole image data, cutting data from drilling cuttings analyzed in drilling fluid, hydraulic fracturing data, petrographic images (142), core sample data, seismic data, reservoir data (159), such as porosity data and permeability data, and/or other types of data to generate and/or update one or more geological models (170), such as models for an unconventional reservoir. Borehole image data may be based on electrical and/or acoustic logging techniques, for example. Geological models may include geochemical or geomechanical models that describe structural relationships within a particular geological region. Cuttings data may describe an analysis or rock typing performed on drill cuttings from a drilling operation, such as using visual methods of describing rock and pore characteristics. Hydraulic fracturing data may describe parameters of one or more hydraulic fracturing operations and associated acquired data, such as measurements relating to any induced fractures and any related results. These different data types may be acquired during exploration, reservoir characterization, hydraulic fracturing, and production operations.

Keeping with the reservoir simulator (160), a reservoir simulator may be used to perform one or more petrographic image analyses. In some embodiments, a reservoir simulator uses selective search functions (145), clustering functions (150), and other image processing functions to identify and classify rock objects in petrographic images (142). In particular, petrography may describe the study of rocks in thin sections using petrographic images. For example, images may be acquired using an image acquisition system (190), that includes a microscope (191) such as a petrological microscope or a scanning electronic microscope (SEM). Using the microscope (191), the image acquisition system (190) may use a camera device (192) to record images of one or more specimens, such as rock samples, biological specimens, and the like. For petrographic images, a petrological microscope may be employed, which is an instrument that uses polarized light that vibrates in a single plane in order to determine optical properties of rock samples. Likewise, a scanning electron microscope (SEM) may be a type of electron microscope that produces images of a sample by scanning the surface with a focused beam of electrons. The electrons from the SEM may interact with atoms in a particular sample, producing various signals that include information about the surface topography and composition of the sample. Furthermore, a petrographic image analysis may include a systematic classification of one or more rocks disposed in a petrographic image. A petrographic image may include an assemblage of various minerals that have grown and recrystallized at different times, where each crystal may include multiple growth zones that corresponds to various geological events spread out over geologic time.

Keeping with petrographic image analyses, a petrographic image analysis (PIA) may obtain an estimate of permeability (k), porosity (ø), and other reservoir data in a core sample. For example, a petrographic image may be acquired and segmented so that a single light intensity is assigned to different pores and a different light intensity is assigned to rock material, thereby resulting in a binary image. Additionally, a geological model may be determined that statistically relates 2-D geometric parameters measured on a thin section to 3-D petrophysical properties. Likewise, an image acquisition system for a petrographic image analysis may include hardware and/or software that acquires and/or processes petrographic images, such as binarized images, high-resolution resin impregnated thin-section scans, and backscattered electron imaging mode (BSEM) photographs, and cathodoluminescence (CL) photomicrographs. For example, a high-resolution thin-section scanned image (HRTSI) of a complete thin-section may be captured using automated microscopy equipment and analyzed for mesoporosity and macroporosity estimation. BSEM images may capture micropores in mud-dominated samples and data combined with the macroporosity estimation to provide a pore size distribution over several orders of magnitude.

While the reservoir simulator (160) is shown at a well site, in some embodiments, the reservoir simulator (160) may be remote from a well site. In some embodiments, the reservoir simulator (160) is implemented as part of a software platform for the control system (114). The software platform may obtain data acquired by the drilling system (110) and logging system (112) as inputs, which may include multiple data types from multiple data sources. The software platform may aggregate the data from these systems (110, 112) in real time for rapid analysis. In some embodiments, the control system (114), the logging system (112), the reservoir simulator (160), and/or a user device coupled to one of these systems may include a computer system that is similar to the computer system (702) described below with regard to FIG. 7 and the accompanying description.

The logging system (112) may include one or more logging tools (113) for use in generating well logs of the formation (106). For example, a logging tool may be lowered into the wellbore (104) to acquire measurements as the tool traverses a depth interval (130) (e.g., a targeted reservoir section) of the wellbore (104). The plot of the logging measurements versus depth may be referred to as a "log" or "well log". Well log data (141) may provide depth measurements of the wellbore (104) that describe such reservoir characteristics as formation porosity, formation permeability, resistivity, water saturation, and the like. The resulting logging measurements may be stored and/or processed, for example, by the control system (114), to generate corresponding well logs for the well (102). A well log may include, for example, a plot of a logging response time versus true vertical depth (TVD) across the depth interval (130) of the wellbore (104).

Turning to examples of logging techniques, multiple types of logging techniques are available for determining various reservoir characteristics. In some embodiments, gamma ray logging is used to measure naturally occurring gamma radiation to characterize rock or sediment regions within a wellbore. In particular, different types of rock may emit different amounts and different spectra of natural gamma radiation. For example, gamma ray logs may distinguish between shales and sandstones/carbonate rocks because radioactive potassium may be common to shales. Likewise, the cation exchange capacity of clay within shales may also result in higher absorption of uranium and thorium further increasing the amount of gamma radiation produced by shales.

Turning to coring, reservoir characteristics may be determined using core sample data acquired from a well site. For example, certain reservoir characteristics can be determined via coring (e.g., physical extraction of rock specimens) to produce core specimens and/or logging operations (e.g., wireline logging, logging-while-drilling (LWD) and measurement-while-drilling (MWD)). Coring operations may include physically extracting a rock specimen from a region of interest within the wellbore (104) for detailed laboratory analysis. For example, when drilling an oil or gas well, a coring bit may cut core plugs (or "cores" or "core specimens") from the formation (106) and bring the core plugs to the surface, and these core specimens may be analyzed at the surface (e.g., in a lab) to determine various characteristics of the formation (106) at the location where the specimen was obtained.

Turning to various coring technique examples, conventional coring may include collecting a cylindrical specimen of rock from the wellbore (104) using a core bit, a core barrel, and a core catcher. The core bit may have a hole in its center that allows the core bit to drill around a central cylinder of rock. Subsequently, the resulting core specimen may be acquired by the core bit and disposed inside the core barrel. More specifically, the core barrel may include a special storage chamber within a coring tool for holding the core specimen. Furthermore, the core catcher may provide a grip to the bottom of a core and, as tension is applied to the drill string, the rock under the core breaks away from the undrilled formation below coring tool. Thus, the core catcher may retain the core specimen to avoid the core specimen falling through the bottom of the drill string. In some embodiments, a micro computed tomography (micro-CT) scan is performed on a core sample. Several types of micro-CT scanning may be used, such as a desktop micro-CT scanner that uses an X-ray generation tube, and a synchrotron X-ray micro-tomography. In particular, a micro-CT scanner may use various X-rays to penetrate from different viewpoints in a core sample to produce an attenuated projection profile that is used for later reconstruction using a filtered back projection algorithm.

Keeping with FIG. 1, geosteering may be used to position the drill bit or drill string of the drilling system (110) relative to a boundary between different subsurface layers (e.g., overlying, underlying, and lateral layers of a pay zone) during drilling operations. In particular, geological model may be used by the drilling system (110) for steering the drill bit in the direction of desired hydrocarbon concentrations. In some embodiments, a well path of a wellbore (104) may be updated by the control system (114) using a geological model. For example, a control system (114) may communicate geosteering commands to the drilling system (110) based on well log data updates or predicted hydrocarbon data that are further adjusted by the reservoir simulator (160) using a geological model. As such, the control system (114) may generate one or more control signals for drilling equipment (or a logging system may generate for logging equipment) based on an updated well path design and/or an updated geological model. As such, a geosteering system may use various sensors located inside or adjacent to the drill string to determine different rock formations within a well path. In some geosteering systems, drilling tools may use resistivity or acoustic measurements to guide the drill bit during horizontal or lateral drilling.

Figure 2:
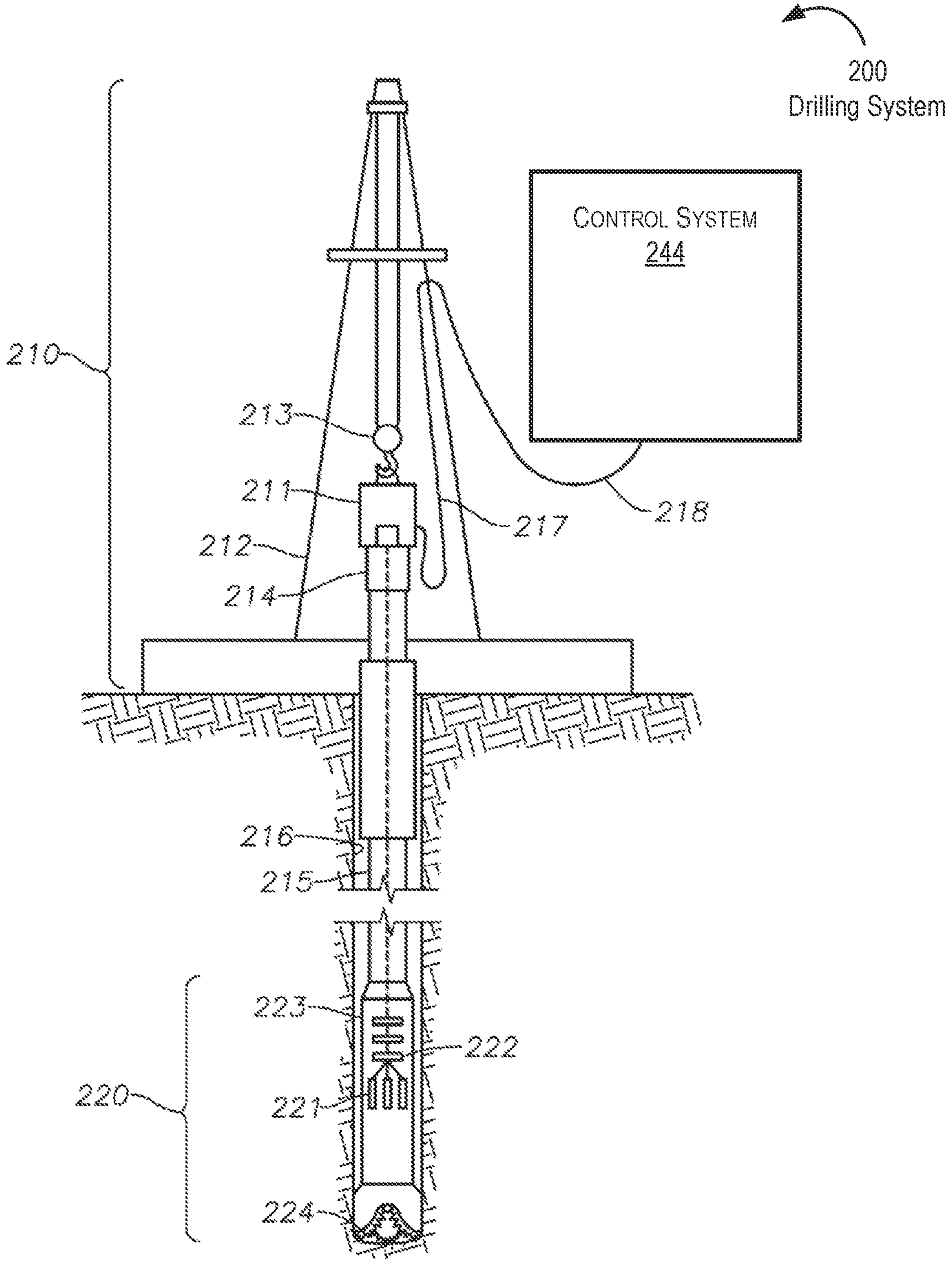

Turning to FIG. 2, FIG. 2 illustrates a system in accordance with one or more embodiments. As shown in FIG. 2, a drilling system (200) may include a top drive drill rig (210) arranged around the setup of a drill bit logging tool (220). A top drive drill rig (210) may include a top drive (211) that may be suspended in a derrick (212) by a travelling block (213). In the center of the top drive (211), a drive shaft (214) may be coupled to a top pipe of a drill string (215), for example, by threads. The top drive (211) may rotate the drive shaft (214), so that the drill string (215) and a drill bit logging tool (220) cut the rock at the bottom of a wellbore (216). A power cable (217) supplying electric power to the top drive (211) may be protected inside one or more service loops (218) coupled to a control system (244). As such, drilling fluid may be pumped into the wellbore (216) using the drive shaft (214) and/or the drill string (215). Likewise, the drilling system may also include a mud pump, a mud line, mud pits, a mud return, and other components related to the circulation or recirculation of drilling fluid within the wellbore (216). The control system (244) may be similar to various control systems described above in FIG. 1 and the accompanying description.

In some embodiments, the drilling system (200) includes a bottomhole assembly (BHA). The bottomhole assembly may refer to a lower portion of the drill string (215) that includes a drill bit (224), bit sub (i.e., a substitute adapter), and a drill collar. The bottomhole assembly may also include a mud motor, stabilizers, heavy-weight drillpipe, jarring devices ("jars"), crossovers for various threadforms, directional drilling and measuring equipment, measurements-while-drilling tools, logging-while-drilling tools and other specialized devices. The bottomhole assembly may produce force for the drill bit to break rock and provide the drilling system with directional control of a wellbore. Different types of bottomhole assemblies may be used, such as a rotary assembly, a fulcrum assembly, and a pendulum assembly.

Moreover, when completing a well, casing may be inserted into the wellbore (216). The sides of the wellbore (216) may require support, and thus the casing may be used for supporting the sides of the wellbore (216). As such, a space between the casing and the untreated sides of the wellbore (216) may be cemented to hold the casing in place. The cement may be forced through a lower end of the casing and into an annulus between the casing and a wall of the wellbore (216). More specifically, a cementing plug may be used for pushing the cement from the casing. For example, the cementing plug may be a rubber plug used to separate cement slurry from other fluids, reducing contamination and maintaining predictable slurry performance. A displacement fluid, such as water, or an appropriately weighted drilling fluid, may be pumped into the casing above the cementing plug. This displacement fluid may be pressurized fluid that serves to urge the cementing plug downward through the casing to extrude the cement from the casing outlet and back up into the annulus.

As further shown in FIG. 2, sensors (221) may be included in a sensor assembly (223), which is positioned adjacent to a drill bit (224) and coupled to the drill string (215). Sensors (221) may also be coupled to a processor assembly that includes a processor, memory, and an analog-to-digital converter (222) for processing sensor measurements. For example, the sensors (221) may include acoustic sensors, such as accelerometers, measurement microphones, contact microphones, and hydrophones. Likewise, the sensors (221) may include other types of sensors, such as transmitters and receivers to measure resistivity, gamma ray detectors, etc. The sensors (221) may include hardware and/or software for generating different types of well logs (such as acoustic logs or density logs) that may provide well data about a wellbore, including porosity of wellbore sections, gas saturation, bed boundaries in a geologic formation, fractures in the wellbore or completion cement, and many other pieces of information about a formation. If such well data is acquired during drilling operations (i.e., logging-while-drilling), then the information may be used to make adjustments to drilling operations in real-time. Such adjustments may include rate of penetration (ROP), drilling direction, altering mud weight, and many others drilling parameters.

In some embodiments, acoustic sensors may be installed in a drilling fluid circulation system of a drilling system (200) to record acoustic drilling signals in real-time. Drilling acoustic signals may transmit through the drilling fluid to be recorded by the acoustic sensors located in the drilling fluid circulation system. The recorded drilling acoustic signals may be processed and analyzed to determine well data, such as lithological and petrophysical properties of the rock formation. This well data may be used in various applications, such as steering a drill bit using geosteering, casing shoe positioning, etc.

The control system (244) may be coupled to the sensor assembly (223) in order to perform various program functions for up-down steering and left-right steering of the drill bit (224) through the wellbore (216). More specifically, the control system (244) may include hardware and/or software with functionality for geosteering a drill bit through a formation in a lateral well using sensor signals, such as drilling acoustic signals or resistivity measurements. For example, the formation may be a reservoir region, such as a pay zone, bed rock, or cap rock.

Turning to geosteering, geosteering may be used to position the drill bit (224) or drill string (215) relative to a boundary between different subsurface layers (e.g., overlying, underlying, and lateral layers of a pay zone) during drilling operations. In particular, measuring rock properties during drilling may provide the drilling system (200) with the ability to steer the drill bit (224) in the direction of desired hydrocarbon concentrations. As such, a geosteering system may use various sensors located inside or adjacent to the drill string (215) to determine different rock formations within a well path. In some geosteering systems, drilling tools may use resistivity or acoustic measurements to guide the drill bit (224) during horizontal or lateral drilling.

Returning to FIG. 1, a reservoir simulator (160) may include hardware and/or software with functionality for generating and/or updating one or more machine-learning models (165) for use in analyzing the formation (106). For example, the reservoir simulator (160) may store well logs and petrographic images (142), and further analyze the well log data, the core sample data, seismic data, and/or other types of data to generate and/or update one or more machine-learning models (165) and/or one or more geological models (170). Thus, different types of machine-learning models may be trained, such as convolutional neural networks, U-Net models, deep neural networks, recurrent neural networks, support vector machines, decision trees, inductive learning models, deductive learning models, supervised learning models, unsupervised learning models, reinforcement learning models, etc. In some embodiments, two or more different types of machine-learning models are integrated into a single machine-learning architecture, e.g., a machine-learning model may include decision trees and neural networks. In some embodiments, the reservoir simulator (160) may generate augmented or synthetic data to produce a large amount of interpreted data for training a particular model.

With respect to support vector machines, a support vector machines may be a machine-learning model that is trained using a supervised machine-learning algorithm. For example, a support vector machine may provide a data analysis on various input features that implement a classification and regression analysis. More specifically, a support vector machine may determine a hyperplane that separates a dataset into different classes, and also determines various points (i.e., support vectors) that lie closest to different classes. Additionally, a support vector machine may use one or more kernel functions to transform data into a desired form for further processing. The term “Kernel” may refer to a set of mathematical functions that provide the window to manipulate the input data. In other words, a kernel function may transform a training set of data so that a non-linear decision surface is able to transform to a linear equation into a higher number of dimension spaces. Examples of kernel functions may include gaussian kernel functions, gaussian kernel radial basis functions (RBFs), sigmoid kernel functions, polynomial kernel functions, and linear kernel functions.

With respect to artificial neural networks, for example, a neural network may include one or more hidden layers, where a hidden layer includes one or more neurons. A neuron may be a modelling node or object that is loosely patterned on a neuron of the human brain. In particular, a neuron may combine data inputs with a set of coefficients, i.e., a set of network weights for adjusting the data inputs. These network weights may amplify or reduce the value of a particular data input, thereby assigning an amount of significance to various data inputs for a task being modeled. Through machine learning, a neural network may determine which data inputs should receive greater priority in determining one or more specified outputs of the neural network. Likewise, these weighted data inputs may be summed such that this sum is communicated through a neuron’s activation function to other hidden layers within the neural network. As such, the activation function may determine whether and to what extent an output of a neuron progresses to other neurons where the output may be weighted again for use as an input to the next hidden layer.

Turning to convolutional neural networks, a convolutional neural network (CNN) is a type of artificial neural network that may be used in computer vision and image recognition, e.g., for processing pixel data. For example, a convolutional neural network may include functionality for performing an application of a filter to an input (e.g., an input image) that results in a particular activation, where repeated filter application may result in an output map of activations called a feature map. A feature map may indicate the locations and strength of one or more detected features in the input to the convolutional neural network. Thus, a convolutional neural network may have the ability to automatically learn multiple filters in parallel specific to a training dataset under the constraints of a specific predictive modeling problem, such as image classification.

In some embodiments, a reservoir simulator (160) uses one or more ensemble learning methods in connection to the machine-learning models (165). For example, an ensemble learning method may use multiple types of machine-learning models to obtain better predictive performance than available with a single machine-learning model. In some embodiments, for example, an ensemble architecture may combine multiple base models to produce a single machine-learning model. One example of an ensemble learning method is a BAGGing model (i.e., BAGGing refers to a model that performs Bootstrapping and Aggregation operations) that combines predictions from multiple neural networks to add a bias that reduces variance of a single trained neural network model. Another ensemble learning method includes a stacking method, which may involve fitting many different model types on the same data and using another machine-learning model to combine various predictions. In some embodiments, two or more different types of machine-learning models are integrated into a single machine-learning architecture, e.g., a machine-learning model may include support vector machines and neural networks. In some embodiments, a reservoir simulator may generate augmented data or synthetic data to produce a large amount of interpreted data for training a particular model.

In some embodiments, various types of machine-learning algorithms (e.g., machine-learning algorithm (175)) may be used to train the model, such as a backpropagation algorithm. In a backpropagation algorithm, gradients are computed for each hidden layer of a neural network in reverse from the layer closest to the output layer proceeding to the layer closest to the input layer. As such, a gradient may be calculated using the transpose of the weights of a respective hidden layer based on an error function (also called a "loss function"). The error function may be based on various criteria, such as mean squared error function, a similarity function, etc., where the error function may be used as a feedback mechanism for tuning weights in the machine-learning model.

In some embodiments, a machine-learning model is trained using multiple epochs. For example, an epoch may be an iteration of a model through a portion or all of a training dataset. As such, a single machine-learning epoch may correspond to a specific batch of training data, where the training data is divided into multiple batches for multiple epochs. Thus, a machine-learning model may be trained iteratively using epochs until the model achieves a predetermined criterion, such as predetermined level of prediction accuracy or training over a specific number of machine-learning epochs or iterations. Thus, better training of a model may lead to better predictions by a trained model.

Keeping with artificial neural networks, for example, an artificial neural network may include one or more hidden layers, where a hidden layer includes one or more neurons. A neuron may be a modelling node or object that is loosely patterned on a neuron of the human brain. In particular, a neuron may combine data inputs with a set of coefficients, i.e., a set of network weights for adjusting the data inputs. These network weights may amplify or reduce the value of a particular data input, thereby assigning an amount of significance to various data inputs for a task being modeled. Through machine learning, a neural network may determine which data inputs should receive greater priority in determining one or more specified outputs of the artificial neural network. Likewise, these weighted data inputs may be summed such that this sum is communicated through a neuron's activation function to other hidden layers within the artificial neural network. As such, the activation function may determine whether and to what extent an output of a neuron progresses to other neurons where the output may be weighted again for use as an input to the next hidden layer.

Turning to recurrent neural networks, a recurrent neural network (RNN) may perform a particular task repeatedly for multiple data elements in an input sequence, with the output of the recurrent neural network being dependent on past computations. As such, a recurrent neural network may operate with a memory or hidden cell state, which provides information for use by the current cell computation with respect to the current data input. For example, a recurrent neural network may resemble a chain-like structure of RNN cells, where different types of recurrent neural networks may have different types of repeating RNN cells. Likewise, the input sequence may be time-series data, where hidden cell states may have different values at different time steps during a prediction or training operation. For example, where a deep neural network may use different parameters at each hidden layer, a recurrent neural network may have common parameters in an RNN cell, which may be performed across multiple time steps. To train a recurrent neural network, a supervised learning algorithm such as a backpropagation algorithm may also be used. In some embodiments, the backpropagation algorithm is a backpropagation through time (BPTT) algorithm. Likewise, a BPTT algorithm may determine gradients to update various hidden layers and neurons within a recurrent neural network in a similar manner as used to train various deep neural networks. In some embodiments, a recurrent neural network is trained using a reinforcement learning algorithm such as a deep reinforcement learning algorithm. For more information on reinforcement learning algorithms, see the discussion below.

Embodiments are contemplated with different types of RNNs. For example, classic RNNs, long short-term memory (LSTM) networks, a gated recurrent unit (GRU), a stacked LSTM that includes multiple hidden LSTM layers (i.e., each LSTM layer includes multiple RNN cells), recurrent neural networks with attention (i.e., the machine-learning model may focus attention on specific elements in an input sequence), bidirectional recurrent neural networks (e.g., a machine-learning model that may be trained in both time directions simultaneously, with separate hidden layers, such as forward layers and backward layers), as well as multidimensional LSTM networks, graph recurrent neural networks, grid recurrent neural networks, etc. With regard to LSTM networks, an LSTM cell may include various output lines that carry vectors of information, e.g., from the output of one LSTM cell to the input of another LSTM cell. Thus, an LSTM cell may include multiple hidden layers as well as various pointwise operation units that perform computations such as vector addition.

With respect to region-based convolutional neural networks, a region-based convolutional neural network (R-CNN) may obtain an input image or other image data at an input layer. The R-CNN may then perform a selective search function (e.g., selective search functions (145)) to extract various regions of interest (ROIs), where an ROI may correspond to a predetermined boundary (e.g., such as a particular rectangle) of an object in the input image. For example, an input petrographic image may include a thousand regions of interest (or region proposals) that are being analyzed by the R-CNN. After determining the image data for different regions, respective image data for respective regions may be sent through a neural network to determine various output features, such as whether a particular region proposal corresponds to a rock object or non-rock object. For each region's output features, a collection of support vector machines may operate as classifiers that may be used to determine what type of object is contained within the respective region. Moreover, various regions that are used by an R-CNN may be referred to as 'region proposals' that identify smaller regions of image data that possibly include objects being searched for in the input image data. To reduce the region proposals in the R-CNN, a selective search function may be used accordingly. Moreover, the convolutional neural network and the support vector machines may be trained separately based on their classifying function within the R-CNN.

Furthermore, various types of region-based convolutional neural networks are contemplated. For example, an R-CNN may be a Fast R-CNN, a Faster R-CNN, a Mask R-CNN, or a you-only-look-once (YOLO) network. While a regular R-CNN may independently determine neural network features on each region of interest, a Fast R-CNN may use a neural network only once on an entire image. At the end of the convolutional neural network, an ROIPooling process may be performed, which slices out each region from the network's output tensor, reshapes the output features, and subsequently classifies the reshaped output features, such as to determine lithology parameters or cutting parameters. As in a regular R-CNN, the Fast R-CNN may also use a selective search function or process to generate various region proposals. In a Faster R-CNN, the Faster R-CNN may integrate the ROI generation into the convolutional neural network itself. In a YOLO network, the YOLO network may perform similar to a fully convolutional neural network, by passing the image once through the FCNN and output a particular prediction for a grid that includes bounding boxes and class probabilities for the bounding boxes. In a Mask R-CNN, the Mask R-CNN may include object instance segmentation. Object Instance Segmentation may both detect object classes (e.g., whether a portion of a petrographic image data is complete rock object or no rock objects are present) along with determining a segmenting of a mask for each object instance. Likewise, some machine-learning models are contemplated that perform only semantic segmentation, such as distinguishing between rock objects within petrographic image data, or detecting the presence of other image object types.

While FIGS. 1 and 2 show various configurations of components, other configurations may be used without departing from the scope of the disclosure. For example, various components in FIGS. 1 and 2 may be combined to create a single component. As another example, the functionality performed by a single component may be performed by two or more components.

Figure 3:
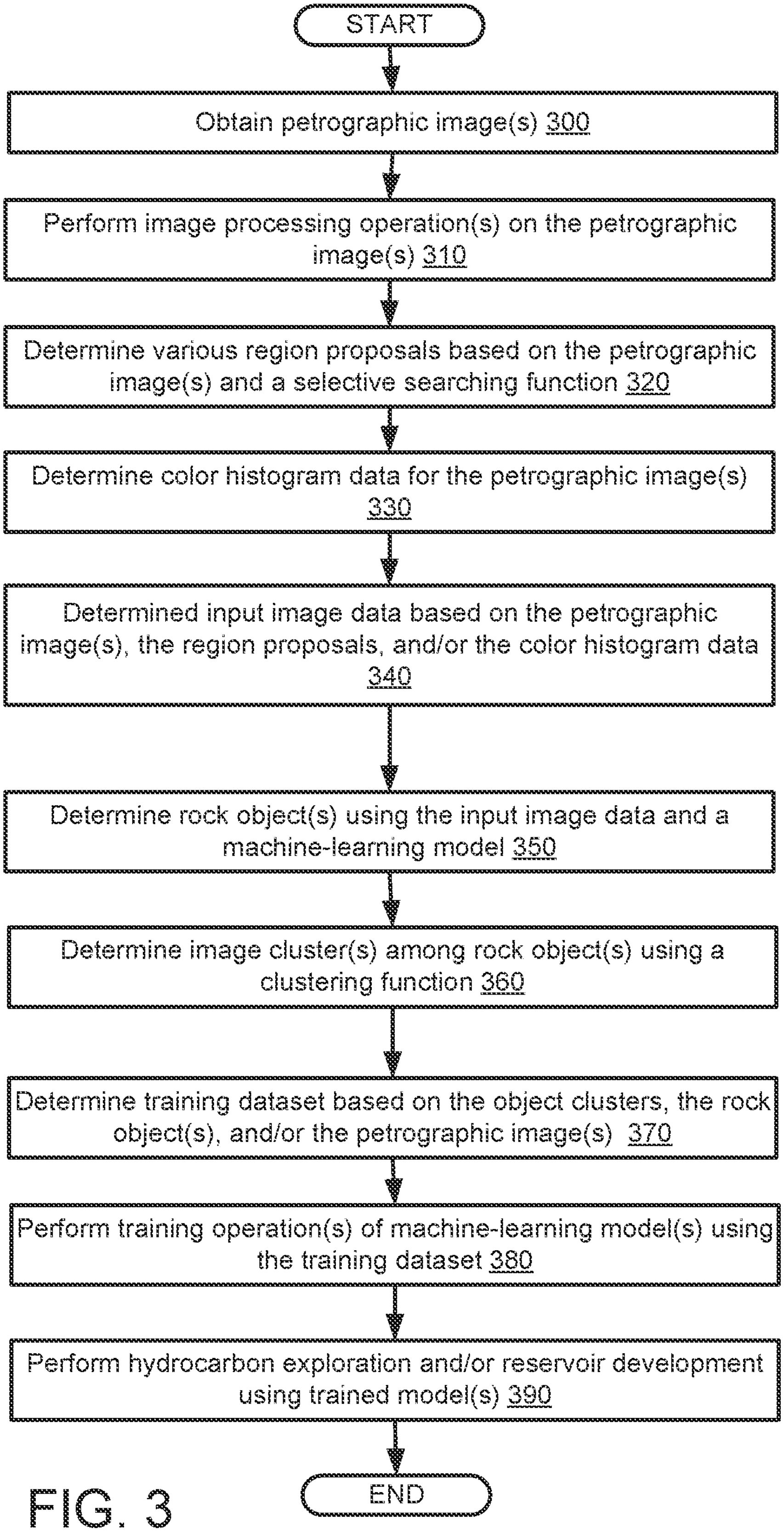
FIG. 3 shows a flowchart in accordance with one or more embodiments.

Turning to FIG. 3, FIG. 3 shows a flowchart in accordance with one or more embodiments. Specifically, FIG. 3 describes a general method for determining rock objects from one or more petrographic images. One or more blocks in FIG. 3 may be performed by one or more components (e.g., reservoir simulator (160), control system (114), control system (244)) as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Figure 4A:
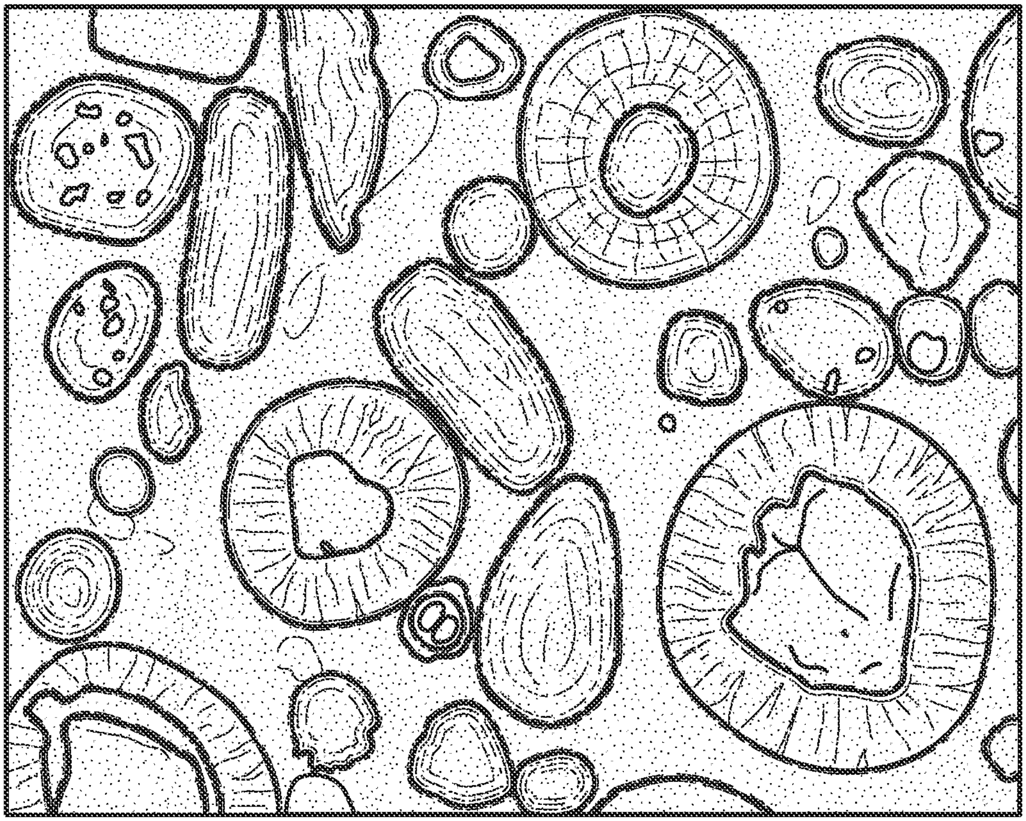
FIGS. 4A, 4B, 4C, 4D, 5, and 6 shows examples in accordance with one or more embodiments.

In Block 300, one or more petrographic images are obtained in accordance with one or more embodiments. A petrographic image may correspond to a thin section rock sample, such as a carbonate rock specimen. Petrographic images may be obtained from several different data sources, such as those from published image-containing literature, online rock image repositories, web scraping, and the like, in order to produce a baseline dataset, such as for training machine-learning models. Likewise, petrographic images may also be obtained using an image acquisition system and from core samples acquired from exploratory wells. An image acquisition system may include a scanning electron microscope or a petrological microscope. FIG. 4A provides an example petrographic image (e.g., petrographic image A (401)) that includes carbonate rocks collected from a journal article data source.

In some embodiments, a petrographic image dataset is collected by scraping individual images using one or more web crawlers. For example, web crawlers may search the Internet for petrographic images that may be classified using the workflow described in FIG. 3. As such, a web crawler may obtain possible image candidates for different categories of carbonate rocks. Likewise, possible petrographic images may be extracted from images in digital journal articles and other scientific literature, e.g., by applying search queries with a targeted list. While petrographic images are described in FIG. 3 and the accompanying description, other image types are also contemplated for use in this workflow. For example, the workflow in FIG. 3 may be used for identifying other candidate objects in an image collection, such as images of biological specimens, other types of geological images, such as images of drill cuttings and digital well logs.

In Block 310, one or more image processing operations are performed on one or more petrographic images in accordance with one or more embodiments. After various petrographic images are collected from one or more data sources, one or more image processing techniques may be applied to individual petrographic images. Examples of image processing operations include edge preserving operations, edge smoothing operations, or operations that increase contrast within the petrographic images. Thus, image processing operations may be performed as one or more preprocessing steps prior to insert image data into a machine-learning workflow. After the image processing techniques, an adjusted image may be produced for further processing or application of various machine-learning techniques. For example, image processing operations may be used to preprocess images to reduce noise that may be present in the original image (e.g., produce an adjusted petrographic image with less background noise). Likewise, image processing operations may also preserve edges without losing overall shape features that are used in later classification processing. In some embodiments, image processing operations include one or more computer vision techniques.

In some embodiments, for example, an image processing operation smoothens an image using a bilateral filter. A bilateral filter may be an image filter that replaces the intensity of each pixel with a weighted average of intensity values from nearby pixels. The weighted average may be based on a Gaussian distribution, for instance.

Figure 4B:
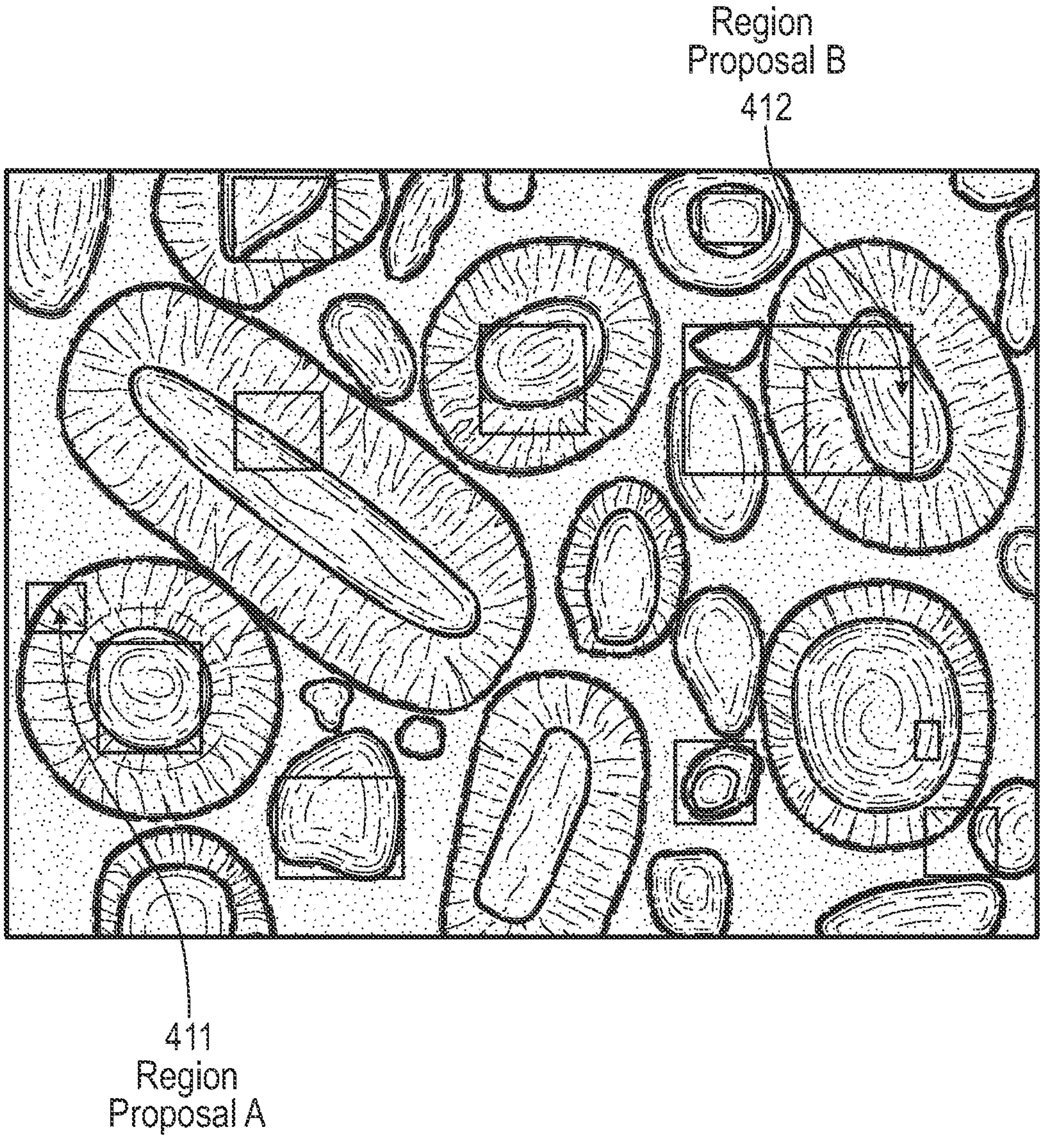

In Block 320, various region proposals are determined based on one or more petrographic images and a selective searching function in accordance with one or more embodiments. For example, a selective search function may be applied by a reservoir simulator or other computer system to one or more petrographic images to determine or more region proposals or regions of interest in a respective image. A region proposal may specify a subset of image data in one, two, or three dimensions (e.g., when analyzing a three-dimensional image). Various regions proposals may not be chosen on a random basis but may be selected to define a specific set of pixels (e.g., a superpixel or a sub-image that is a portion of the petrographic image) to find different regions that may include an object of interest, such as a rock object or input image features for identifying a particular rock type. This pixel selection process may be a hierarchical process based on various similarity measures, such as a color metric, a texture metric, a size metric (e.g., the size of the potential object in the petrographic image), a shape metric, and a combination of different metrics. FIG. 4B provides an example of various region proposals (e.g., region proposal A (411) and region proposal B (412)) by a selective search function. Examples of selective search functions include various combinatorial algorithms, such as a greedy algorithm or dynamic programming algorithm.

In Block 330, color histogram data are determined for one or more petrographic images in accordance with one or more embodiments. In particular, a color histogram may be a representation of the distribution of various colors in an image. As such, color histogram data may identify the number of pixels, such as in a particular region proposal, that have colors in one or more color ranges, that span the image's color space. For example, color histogram data may describe the number of pixels in a region proposal that correspond to one or more predetermined colors. Examples of color spaces may include red-green-blue (RGB) space or a hue, saturation, and value (HSV) space. Likewise, color spaces may also be based on various optical wavelength ranges inside and/or outside the visible light spectrum.

Figure 4C:
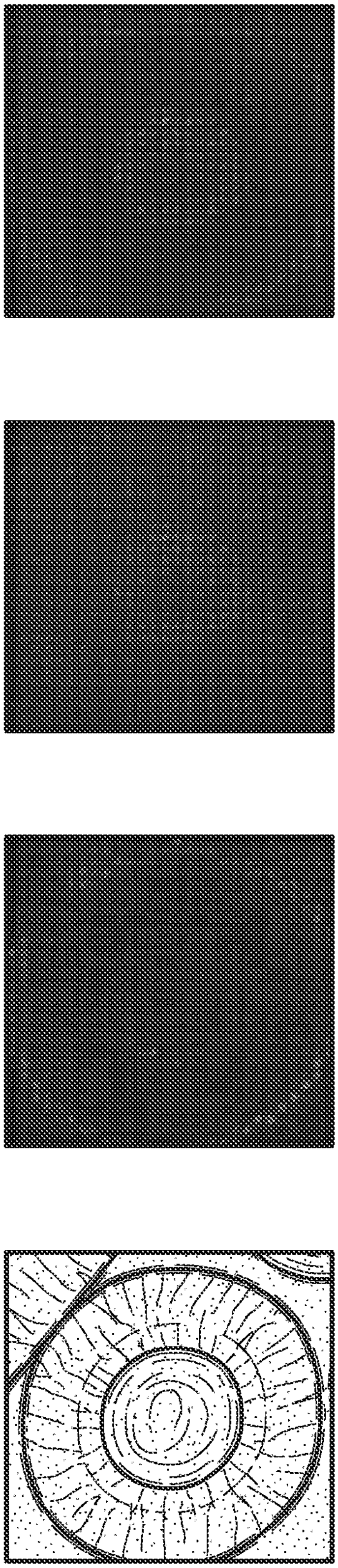

In some embodiments, color histogram data is based on histogram oriented gradients (HOG). For example, color histogram data may identify occurrences of gradient orientation in localized portions of a petrographic image. Image data corresponding to a particular region proposal may be represented by a stack of the Histogram oriented gradients feature descriptors for various channels separately. Histogram oriented gradients may be determined using gradient computation, orientation binning, descriptor blocks, block normalization, and/or object detection. FIG. 4C provides an example of determining HOG feature descriptors extracted from three channels of a region proposal in a petrographic image.

In Block 340, input image data are determined based on one or more petrographic images, various region proposals, and/or color histogram data in accordance with one or more embodiments. For example, various image features may be determined based on color histogram data and/or image data within a predefined region proposal in an image. These image features may be used as input image data that is passed through a machine-learning model at the input layer to determine one or more labels at the output layer, such as whether the region proposal includes a rock object.

In Block 350, one or more rock objects are determined using input image data and a machine-learning model in accordance with one or more embodiments. In some embodiments, for example, the machine-learning model is a support vector machine (SVM) that performs a classification based on Histogram Oriented Gradients (HOG) features as the input image data. Thus, a machine-learning model may perform a filtering process that can separate input image data (e.g., a sub-image corresponding to a respective region proposal) that includes a complete rock object from input image data with a partial rock object and/or no rock objects. A one-class SVM classifier may be trained with extracted HOG features or other image features, where the SVM classifier may determine a decision boundary between the predicted presence of a full rock object and partial rock object or no rock objects.

Moreover, some embodiments provide one or more techniques that collect and extract individual rock objects from various petrographic images and/or other images. For example, a reservoir simulator or an image acquisition system may determine whether input image data for a particular region proposal is positive (i.e., includes a complete rock object or a partial rock object) or negative (i.e., includes no rock object). The negative region proposals may be discarded accordingly, while positive region proposals may be added to a dataset for further processing.

Figure 5:
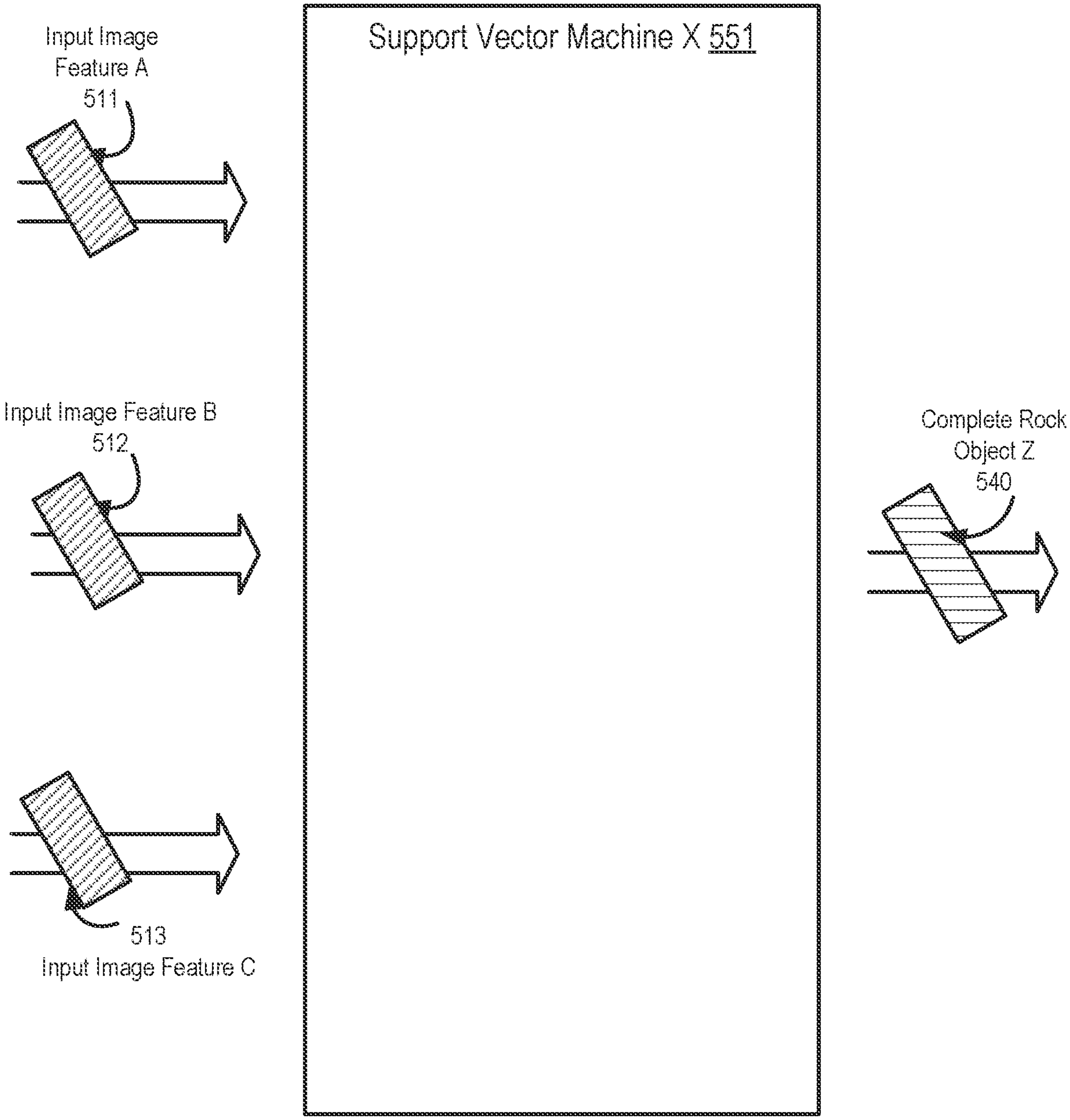

Turning to FIG. 5, FIG. 5 provides an example of using a support vector machine to classify rock objects in accordance with one or more embodiments. In FIG. 5, a support vector machine X (551) obtains various input features regarding a petrographic image, i.e., input image feature A (511), input image feature B (512), and input image feature C (513). For example, input image features (511, 512, 513) may correspond to a particular region proposal in a petrographic image, where image data for the region proposal is processed to produce multiple input image features, such as based on a similarity measure such as color histogram metric or other image metric. Using the input image features (511, 512, 513), the support vector machine X (551) determines that the region proposal include a complete rock object Z (540), rather than no rock objects or a partial rock object. While a support vector machine is described in some embodiments, other machine-learning models are contemplated such as artificial neural networks, such as a convolution neural network or a region-based convolution neural network (R-CNN). In particular, Block 320-350 may be integrated into a single machine-learning architecture, such as an R-CNN.

Returning to FIG. 3, in Block 360, one or more image clusters among one or more rock objects using a clustering function in accordance with one or more embodiments. In some embodiments, various image portions with rock objects are grouped using one or more clustering functions. For example, image clusters may be determined with full or partial rock object using an unsupervised clustering algorithm. These image clusters may assist a user in identifying similar classes of rock objects, such as carbonate objects, silicate objects, phosphate objects, sulfide objects, halides objects, and the like. In some embodiments, after classifying full rock objects in one image cluster and partial rock objects in another image cluster, a semi-supervised multiclass labeling framework may be performed on individual images in each image cluster. These image clusters may correspond to different geological rock categories that are used by rock experts. Likewise, a clustering function may also determine whether further cluster splitting or cluster combination are needed. Thus, an automated clustering method may be more efficient than an image-by-image manual labeling process by one or more users. These image clusters may be used to determine automatically a training dataset with both petrographic images and output labels for the purpose of eventually generating and training supervised multiclass petrographic image classification systems. In some embodiments, the image clusters are used by users to manually classify groups to build up a baseline dataset for various machine-learning algorithms.

Figure 4D:
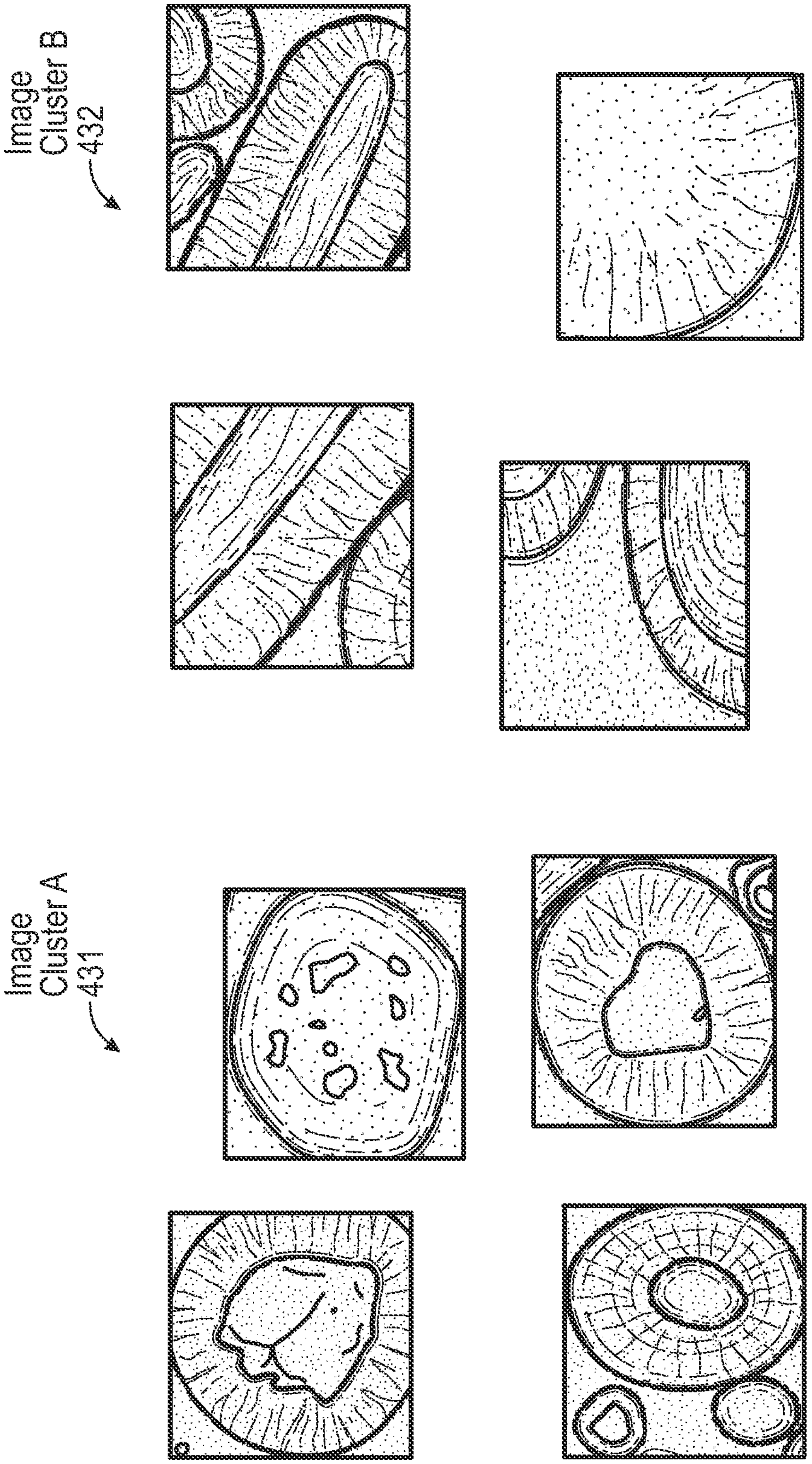

Turning to FIG. 4D, FIG. 4D provides an example of image clusters (i.e., image cluster A (431) and image cluster B (432)) based on image data for various region proposals and a clustering function. Image cluster A (431) includes various sub-images that are identified as having rock objects, while image cluster B (432) includes various sub-images for other region proposals that are being discarded for being classified as lacking any complete rock objects.

Image cluster A (431) in FIG. 4D may be saved as multiple images for inclusion to a rock image dataset.

Returning to FIG. 3, in Block 370, a training dataset is determined based on one or more image clusters, one or more rock objects, and/or one or more petrographic images in accordance with one or more embodiments. In particular, a training dataset may include multiple classified images where a particular classified image has a corresponding label based on one or more image objects. In other words, training data may include a petrographic image as an input and a rock label as the predicted data. Moreover, a classified petrographic image in the dataset may include one or more rock objects, where the classified petrographic image is labeled as having two complete rock objects that are carbonate rock objects. The training dataset may include classified images for training a machine-learning model, such as an artificial neural network or other computer vision model, and testing data for verifying the accuracy of the trained model.

In Block 380, one or more training operations of one or more machine-learning models are performed using a training dataset in accordance with one or more embodiments. For example, the training operations may be similar to one or more training operations described above in FIG. 1 and the accompanying description. In some embodiments, a trained model may predict various rock labels for an input petrographic image. However, other trained models are contemplated using the training dataset, such as machine-learning models that use image data to predict well log data, lithological data, the presence of hydrocarbons deposits in a particular rock sample, water and oil saturation values, and other reservoir data (e.g., porosity or permeability values).

In some embodiments, for example, a machine-learning model may be used in Block 350 of FIG. 3 to determine an image object (e.g., a particular type of rock object) for generating a classified image dataset that can be used for training a different model. The classified image dataset may include both an input image (e.g., an original petrographic image) and one or more corresponding labels (e.g., the original petrographic image include three rock objects that are also carbonate rocks). Likewise, in Block 380, a different machine-learning model may be trained using the classified image dataset, a supervised machine-learning algorithm, and multiple machine-learning epochs. For illustration, multiple support vector machines may be used in Block 350, while a convolution neural network is trained in Block 380 with a backpropagation algorithm to predict porosity data from image data using petrographic images and reservoir data as the input features.

In Block 390, hydrocarbon exploration and/or reservoir development are performed using one or more trained models for a geological region of interest in accordance with one or more embodiments. For example, one or more trained models may be used in drilling operations, stimulation operations (e.g., for hydraulic fracturing), and well path planning to predict data in real-time. Likewise, a trained model may predict data for use in one or more artificial intelligence workflows. In some embodiments, commands are transmitted to various control systems to automate drilling operations or stimulation operations necessary for drilling or completing a well based on predicted data from one or more trained models. Likewise, a user may select different stimulation parameters or adjusted drilling parameters based on predicted data from a trained model. A user selection may be obtained within a graphical user interface.

Furthermore, a geological region of interest may be a portion of a geological area or volume that includes one or more wells or formations of interest desired or selected for further analysis, e.g., for determining a location of hydrocarbons deposits or reservoir development purposes for a respective reservoir. As such, a geological region of interest may include one or more reservoir regions in an unconventional reservoir selected for running simulations.

Figure 6:
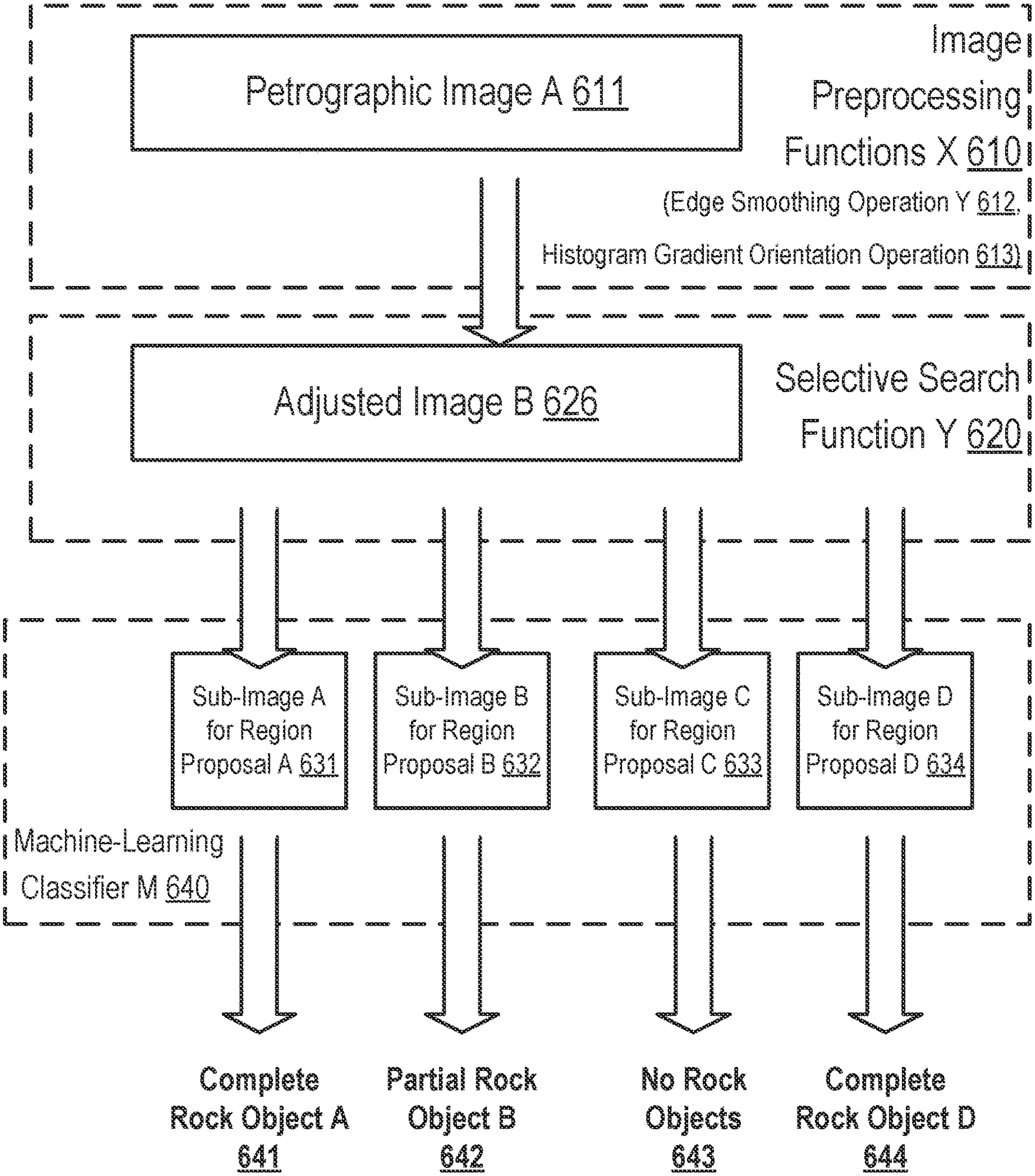

Turning to FIG. 6, FIG. 6 shows an example of determining rock objects in a petrographic image using a machine-learning classifier in accordance with one or more embodiments. In FIG. 6, an image acquisition system (not shown) acquires a petrographic image A (611) using a petrologic microscope. Afterwards, the image acquisition system transmits the petrographic image A (611) to a computer system, such as a reservoir simulator for further processing. In particular, the computer system applies image preprocessing functions X (610) to the petrographic image A (611) to produce an adjusted image B (626). The image preprocessing functions include an edge smoothing operation (612) as well as a histogram gradient orientation operation (613). While the histogram gradient orientation operation (613) is applied as a preprocessing step, it may also be applied to image data for various region proposals in the petrographic image A (611) or the adjusted image B (626).

Keeping with FIG. 6, a selective search function Y (620) is applied to the adjusted image B (626). In particular, the selective search function Y (620) determines various region proposals for dividing image data within the adjusted image B (626) into possible regions of interest. In particular, the selective search function Y (620) determines sub-image A (631) for region proposal A, sub-image B (632) for region proposal B, sub-image C (633) for region proposal C, and sub-image D (634) for region proposal D. Afterwards, the sub-images (631, 532, 533, 534) are passed through a machine-learning classifier M (640), which may be one or more support vector machines as well as one or more artificial neural networks. More specifically, the machine-learning classifier M (640) analyzes a sub-image to determine whether the sub-image includes a complete rock object, such as a carbonate rock, a partial rock object where a portion of the rock is missing from the sub-image, or no rock objects are present in the sub-image. Thus, the machine-learning classifier M (640) determine that sub-image A (631) includes a complete rock object A (641), sub-image B (632) includes a partial rock object B (642), sub-image C (633) include no rock objects (643), and sub-image D (634) includes a complete rock object D (644), respectively.

Figure 7:
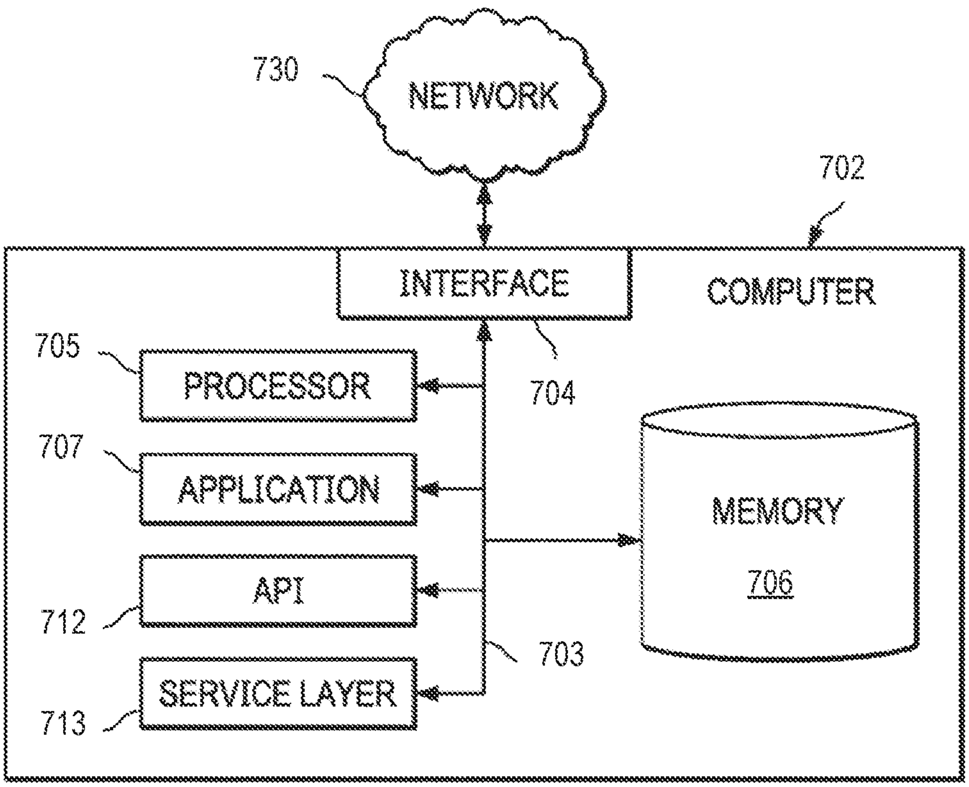
FIG. 7 shows a computer system in accordance with one or more embodiments.

Embodiments may be implemented on a computer system. FIG. 7 is a block diagram of a computer system (702) used to provide computational functionalities associated with described algorithms, methods, functions, processes, flows, and procedures as described in the instant disclosure, according to an implementation. The illustrated computer (702) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730) or cloud. In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) or cloud from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or other suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704 includes logic encoded in software or hardware (or a combination of software and hardware) and operable to communicate with the network (730) or cloud. More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), each computer (702) communicating over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

In some embodiments, the computer (702) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, a cloud computing system may operate according to one or more service models, such as infrastructure as a service (IaaS), platform as a service (PaaS), software as a service (SaaS), mobile "backend" as a service (MBaaS), artificial intelligence as a service (AIaaS), serverless computing, and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method, comprising:
obtaining a first petrographic image;
determining, by a computer processor, a first plurality of region proposals based on the first petrographic image and a selective search function, wherein a respective region proposal among the first plurality of region proposals corresponds to a plurality of pixels in the first petrographic image according to at least one predetermined dimension;
determining, by the computer processor, color histogram data for the first petrographic image;
determining, by the computer processor, input image data based on the first petrographic image, the first plurality of region proposals, and the color histogram data; and
determining, by the computer processor, one or more rock objects using the input image data and a first machine-learning model,
wherein the selective search function is a hierarchical process based on one or more similarity measures selected from a group consisting of a color metric, a texture metric, a size metric, and a shape metric.

2. The method of claim 1, further comprising:
determining, using the one or more rock objects, a first classified image based on the first petrographic image;
determining a training dataset based on a plurality of classified images and the first classified image;
obtaining a second machine-learning model; and
training the second machine-learning model using the training dataset, a plurality of machine-learning epochs, and a supervised learning algorithm.

3. The method of claim 1, further comprising:
obtaining a plurality of petrographic images;
determining a second plurality of region proposals based on the plurality of petrographic images and the selective search function;
obtaining training data comprising a plurality of classified images based on the plurality of petrographic images and the second plurality of region proposals; and
performing a training operation on a second machine-learning model using the training data,
wherein the second machine-learning model determines one or more predicted rock labels for a respective input petrographic image, and
wherein second machine-learning model is updated iteratively until the one or more predicted rock labels satisfy a predetermined criterion.

4. The method of claim 1,
wherein the color histogram data comprises a plurality of histogram oriented gradients,
wherein the first machine-learning model is a support vector machine, and
wherein the support vector machine uses the plurality of histogram oriented gradients and a kernel function to determine the one or more rock objects.

5. The method of claim 1,
wherein the selective search function determines a respective region proposal among the first plurality of region proposals for an image object of interest within a respective petrographic image, and
wherein the respective region proposal corresponds to a set of pixels that form a sub-image.

6. The method of claim 1, further comprising:
obtaining a plurality of petrographic images;
determining a plurality of rock objects from the plurality of petrographic images using the first machine-learning model;
determining one or more image clusters using the plurality of rock objects and a clustering function; and
determining a training dataset based on the one or more image clusters.

7. The method of claim 6,
wherein the clustering function is an unsupervised machine-learning algorithm.

8. The method of claim 1,
wherein the first machine-learning model is an artificial neural network comprising an input layer, a plurality of hidden layers, and an output layer.

9. The method of claim 1,
wherein the first petrographic image is acquired using a petrological microscope.

10. The method of claim 1, further comprising:
determining predicted data for a geological region of interest using one or more petrographic images and a second machine-learning model, wherein the second machine-learning model is trained using a training dataset comprising the first petrographic image and the one or more rock objects; and
determining a presence of hydrocarbon deposits using the predicted data.

11. A method comprising:
obtaining a first petrographic image;
determining, by a computer processor, a first plurality of region proposals based on the first petrographic image and a selective search function, wherein a respective region proposal among the first plurality of region proposals corresponds to a plurality of pixels in the first petrographic image according to at least one predetermined dimension performing an edge smoothing operation on the first petrographic image to produce an adjusted petrographic image,
determining, by the computer processor, color histogram data using the adjusted petrographic image;
determining, by the computer processor, input image data based on the first petrographic image, the first plurality of region proposals, and the color histogram data; and
determining, by the computer processor, one or more rock objects using the input image data and a first machine-learning model.

12. A system, comprising:
an image acquisition system comprising a camera device; and
a reservoir simulator coupled to the image acquisition system, wherein the reservoir simulator comprises a computer processor, the reservoir simulator is configured to perform a method comprising:
acquiring, using the image acquisition system, a first petrographic image;
determining a first plurality of region proposals based on the first petrographic image and a selective search function, wherein a respective region proposal among the first plurality of region proposals corresponds to a plurality of pixels in the first petrographic image according to at least one predetermined dimension;

determining color histogram data for the first petrographic image;

determining input image data based on the first petrographic image, the first plurality of region proposals, and the color histogram data;

determining one or more rock objects using the input image data and a first machine-learning model;

determining predicted data for a geological region of interest using one or more petrographic images and a second machine-learning model, wherein the second machine-learning model is trained using a training dataset comprising the first petrographic image and the one or more rock objects; and determining a presence of hydrocarbon deposits using the predicted data.

13. The system of claim 12, wherein the image acquisition system comprises a petrological microscope.

14. The system of claim 12, wherein the method further comprises:

determining, using the one or more rock objects, a first classified image based on the first petrographic image;

determining a training dataset based on a plurality of classified images and the first classified image;

obtaining a second machine-learning model; and training the second machine-learning model using the training dataset, a plurality of machine-learning epochs, and a supervised learning algorithm.

15. The system of claim 12, wherein the color histogram data comprises a plurality of histogram oriented gradients, wherein the first machine-learning model is a support vector machine, and wherein the support vector machine uses the plurality of histogram oriented gradients and a kernel function to determine the one or more rock objects.

16. The system of claim 12, wherein the selective search function determines a respective region proposal among the first plurality of region proposals for an image object of interest within a respective petrographic image, and wherein the respective region proposal corresponds to a set of pixels that form a sub-image.

17. The system of claim 12, wherein the method further comprises:

obtaining a plurality of petrographic images;

determining a second plurality of region proposals based on the plurality of petrographic images and the selective search function;

obtaining training data comprising a plurality of classified images based on the plurality of petrographic images and the second plurality of region proposals; and performing a training operation on a second machine-learning model using the training data, wherein the second machine-learning model determines one or more predicted rock labels for a respective input petrographic image, and wherein second machine-learning model is updated iteratively until the one or more predicted rock labels satisfy a predetermined criterion.

18. The system of claim 12, further comprising:

a drilling system; and a control system coupled to the drilling system and the reservoir simulator, wherein the control system is configured to transmit a command to the drilling system to perform a drilling operation based on predicted data for a geological region of interest, and wherein the predicted data is determined using a trained model that is trained using a training dataset comprising a classified petrographic image corresponding to the first petrographic image and the one or more rock objects.

* * * * *